US00PP15689P2

(12) United States Plant Patent
de Bont

(10) Patent No.: US PP15,689 P2
(45) Date of Patent: Mar. 22, 2005

(54) ***ANTIRRHINUM* PLANT NAMED 'SANT229A'**

(50) Latin Name: *Antirrhinum×hybrida*
Varietal Denomination: Sant229A

(75) Inventor: Diony de Bont, Alphen aan den Rijn (NL)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 10/862,857

(22) Filed: Jun. 7, 2004

(51) Int. Cl.[7] ..... A01H 5/00
(52) U.S. Cl. ..... Plt./322
(58) Field of Search ..... Plt./322

*Primary Examiner*—Kent Bell
(74) *Attorney, Agent, or Firm*—C. A. Whealy

(57) ABSTRACT

A new and distinct cultivar of *Antirrhinum* plant named 'Sant229A', characterized by its outwardly spreading, trailing and low mounded plant habit; freely branching habit; dense and bushy growth habit; freely flowering habit; and flowers that are pale purple in color.

1 Drawing Sheet

Botanical classification/cultivar designation: *Antirrhinum×hybrida* cultivar Sant229A.

BACKGROUND OF THE INVENTION

The present Invention relates to a new and distinct cultivar of *Antirrhinum* plant, commercially known as a trailing Snapdragon, botanically known as *Antirrhinum hybrida*, and hereinafter referred to by the cultivar name Sant229A.

The new *Antirrhinum* is a product of a planned breeding program conducted by the Inventor in Alphen aan den Rijn, The Netherlands. The objective of the breeding program is to create new freely flowering *Antirrhinums* with trailing and mounded plant habit, vigorous growth habit, large flowers and attractive leaf and flower coloration.

The new *Antirrhinum* originated from a cross-pollination made by the Inventor in 1999 in Ter Aar, The Netherlands, of an unnamed selection of *Antirrhinum hybrida*, not patented, as the female, or seed parent, with an unnamed selection of *Antirrhinum hybrida*, not patented, as the male, or pollen parent. The new *Antirrhinum* was discovered and selected as a single plant from the resulting progeny of the cross-pollination in a controlled environment in Stavenisse, The Netherlands in 2001.

Asexual reproduction of the new cultivar by terminal vegetative cuttings since 2001, in Ter Aar, The Netherlands has shown that the unique features of this new *Antirrhinum* are stable and reproduced true to type in successive generations.

SUMMARY OF THE INVENTION

Plants of the cultivar Sant229A have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Sant229A'. These characteristics in combination distinguish 'Sant229A' as a new and distinct cultivar:

1. Outwardly spreading, trailing and low mounded plant habit.
2. Freely branching habit; dense and bushy growth habit.

3. Freely flowering habit.
4. Flowers that are pale purple in color.

Plants of the new *Antirrhinum* differ from the parental selections primarily in plant size and vigor.

Plants of the new *Antirrhinum* can be compared to plants of the cultivar Balumpink, disclosed in U.S. Plant Pat. No. 13,596. In side-by-side comparisons conducted in Encinitas, Calif., plants of the new *Antirrhinum* differed primarily from plants of the cultivar Balumpink in flower color as plants of the cultivar Balumpink had pale pink-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Antirrhinum*.

The photograph at the top of the sheet comprises a side perspective view of typical plants of 'Sant229A' grown in a container.

The photograph at the bottom of the sheet is a close-up view of typical flowers and leaves of 'Sant229A'.

DETAILED BOTANICAL DESCRIPTION

Plants of the cultivar Sant229A have not been observed under all possible environmental conditions. The phenotype may vary somewhat with variations in environment such as temperature and light intensity, without, however, any variance in genotype.

The aforementioned photographs and following observations and measurements describe plants grown in Encinitas, Calif., under commercial practice in a polyethylene-covered greenhouse during the winter and spring with day temperatures about 24° C., night temperatures about 18° C. and light levels about 4,000 foot-candles. Plants used for the photographs and description were about 16 weeks from planting rooted cuttings in one-gallon containers with three plants per container. In the following description, color references are made to The Royal Horticultural Society Colour Chart, 1995

Edition, except where general terms of ordinary dictionary significance are used.

Botanical classification: *Antirrhinum hybrida* cultivar Sant229A.

Parentage:

*Female parent*.—Unnamed selection of *Antirrhinum hybrida*, not patented.

*Male parent*.—Unnamed selection of *Antirrhinum hybrida*, not patented.

Propagation:

*Type cutting*.—Terminal vegetative cuttings.

*Time to initiate roots*.—Summer: About 10 days at 21° C. Winter: About 11 days at 20° C.

*Time to develop roots*.—Summer: About 30 days at 21° C. Winter: About 35 days at 20° C.

*Root description*.—Fine, fibrous; white in color.

*Rooting habit*.—Freely branching.

Plant description:

*Form*.—Annual flowering plant; outwardly spreading, trailing and low mounded plant habit. Freely branching habit; dense and bushy growth habit; about seven to eight lateral branches per plant.

*Plant height*.—About 14 cm.

*Plant diameter (area of spread), single plant*.—About 20 cm.

*Vigor*.—Moderate growth rate; vigorous.

*Lateral branches*.—Length: About 25 cm. Diameter: About 2 mm. Internode length, flowering branches: About 1.5 cm. Texture: Pubescent. Color: 144A.

*Foliage description*.—Arrangement: Opposite before flowering; alternate after flowers develop; simple. Length: About 3.4 cm. Width: About 1.5 cm. Shape: Elliptic. Apex: Broadly acute. Base: Attenuate. Margin: Entire. Texture, upper and lower surfaces: Smooth, glabrous. Venation pattern: Pinnate, arcuate. Color: Developing leaves, upper surface: 147A. Developing leaves, lower surface: 147B. Fully expanded leaves, upper surface: 147A. Fully expanded leaves, lower surface: 148B. Venation, upper surface: 147B. Venation, lower surface: 148B. Petiole length: About 1 cm. Petiole diameter: About 1 mm. Petiole color, upper and lower surfaces: 146B.

Flower description:

*Flower type and habit*.—Single bi-labiate personate flowers arranged in loose terminal racemes. Freely flowering habit, usually about four to five open flowers and about three to four flower buds per raceme. Flowers face mostly outwardly or drooping. Flowers not persistent. Flowers not fragrant.

*Natural flowering season*.—Long flowering period, spring until autumn; flowering continuous during this period. Plants start flowering about twelve weeks after planting rooted cuttings.

*Flower longevity*.—Flowers last about one week on the plant.

*Inflorescence length*.—About 8.9 cm.

*Inflorescence diameter*.—About 4.5 cm.

*Flower length*.—About 2.4 cm.

*Flower width*.—About 2 cm.

*Flower depth*.—About 3.5 cm.

*Flower buds*.—Length: About 1.3 cm. Diameter: About 7 mm. Shape: Ovoid. Color: Towards the base, 145D; mid-section and apex, 186C.

*Corolla*.—Shape/arrangement: Broadly tubular; five modified petals; upper two and lower three petals fused. Petal lobe apices: Rounded. Petal lobe margin: Entire. Length, upper petal lobes: About 2.2 cm. Length, lower petal lobes: About 1.4 cm. Width, upper petal lobes: About 1.2 cm. Width, lower petals lobes: About 1 cm. Texture, upper and lower surfaces of petal lobes: Slightly pubescent; velvety. Texture, throat: Pubescent. Color: When opening, upper petal lobes, upper surface: 186C. When opening, lower petal lobes, upper surface: 186D; bulge, 3A. When opening, all petal lobes, lower surface: 155A tinted with 186D. Fully opened, upper petal lobes, upper surface: 186C to 186D; longitudinal stripes, 186A to 186B; color becoming closer to 155A tinted with 75D with development. Fully opened, lower petal lobes and tube, upper surface: 155A; bulge, 3A. Fully opened, all petal lobes and tube, lower surface: 155A tinted with 186D.

*Sepals*.—Quantity/arrangement: Five per flower; fused at base. Length: About 6 mm. Width: About 3 mm. Shape: Elliptic. Apex: Broadly acute. Margin: Entire. Texture, upper and lower surfaces: Densely pubescent. Color, upper and lower surfaces: 146A.

*Pedicels*.—Length: About 7 mm. Diameter: About 1 mm. Strength: Moderately strong; flexible. Angle: About 15° from the stem. Color: 144B.

*Reproductive organs*.—Androecium: Stamen quantity: Four per flower. Anther length: About 1 mm. Anther shape: Oval, bi-lobed. Anther color: 10B. Pollen amount: Moderate to scarce. Pollen color: 12C. Gynoecium: Pistil quantity: One per flower. Pistil length: About 1.8 cm. Style length: About 1.4 cm. Style color: 157A. Stigma color: 145C. Ovary color: 145D.

*Seeds/fruits*.—Seed and fruit development has not been observed.

Disease/pest resistance: Plants of the new *Antirrhinum* have not been observed to be resistant to pathogens and pests common to *Antirrhinum*.

Temperature tolerance: Plants of the new *Antirrhinum* have been observed to tolerate temperatures from −5 to 32° C.

It is claimed:

1. A new and distinct cultivar of *Antirrhinum* plant named 'Sant229A', as illustrated and described.

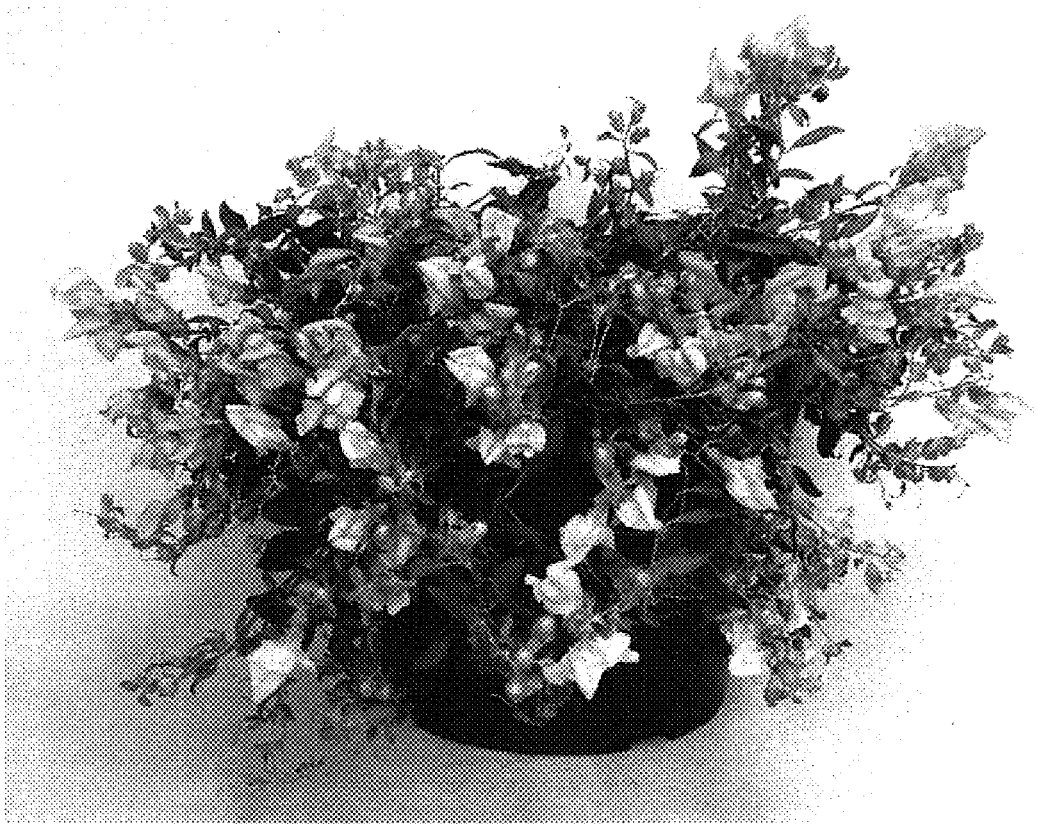
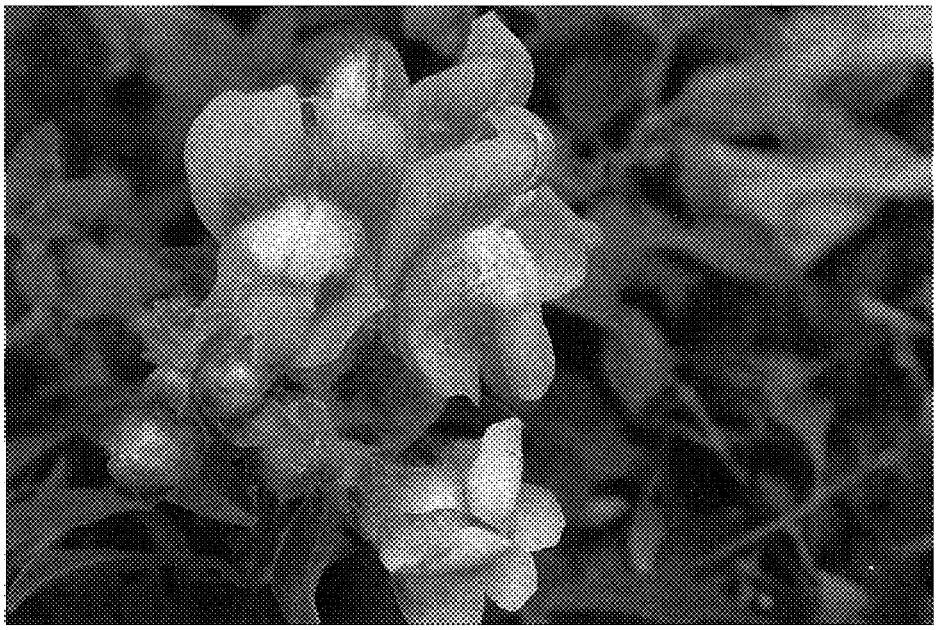

* * * * *